(12) United States Patent
Boismier

(10) Patent No.: US 7,955,313 B2
(45) Date of Patent: Jun. 7, 2011

(54) COMPOSITE CATHETER BRAID

(75) Inventor: Dennis A. Boismier, Shorewood, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2052 days.

(21) Appl. No.: 10/738,854

(22) Filed: Dec. 17, 2003

(65) Prior Publication Data

US 2005/0137519 A1 Jun. 23, 2005

(51) Int. Cl.
*A61M 25/00* (2006.01)
(52) U.S. Cl. ......................... 604/527; 604/524
(58) Field of Classification Search ............. 604/103.01, 604/523, 524, 526, 527
See application file for complete search history.

(56) References Cited

U.S. PATENT DOCUMENTS

| | | |
|---|---|---|
| 3,416,531 A | 12/1968 | Edwards |
| 3,485,234 A | 12/1969 | Stevens |
| 3,558,754 A | 1/1971 | Martin |
| 3,612,058 A | 10/1971 | Ackerman |
| 4,210,478 A | 7/1980 | Shoney |
| 4,279,252 A | 7/1981 | Martin |
| 4,419,095 A | 12/1983 | Nebergall et al. |
| 4,425,919 A | 1/1984 | Alston, Jr. et al. |
| 4,447,239 A | 5/1984 | Krutten |
| 4,495,134 A | 1/1985 | Ouchi et al. |
| 4,516,970 A | 5/1985 | Kaufman et al. |
| 4,516,972 A | 5/1985 | Samson |
| 4,531,943 A | 7/1985 | Van Tassel et al. |
| 4,571,240 A | 2/1986 | Samson et al. |
| 4,577,543 A | 3/1986 | Wilson |
| 4,588,399 A | 5/1986 | Nebergall et al. |
| 4,690,175 A | 9/1987 | Ouchi et al. |
| 4,705,511 A | 11/1987 | Kocak |
| 4,737,153 A | 4/1988 | Shimamura et al. |
| 4,764,324 A | 8/1988 | Burnham |
| 4,817,613 A | 4/1989 | Jaraczewski et al. |
| 4,842,590 A | 6/1989 | Tanabe et al. |
| 4,863,442 A | 9/1989 | DeMello et al. |
| 4,898,591 A | 2/1990 | Jang et al. |
| 4,981,478 A | 1/1991 | Evard et al. |
| 5,017,259 A | 5/1991 | Kohsai |
| 5,018,969 A | 5/1991 | Andreiko et al. |
| 5,019,057 A | 5/1991 | Truckai |

(Continued)

FOREIGN PATENT DOCUMENTS

EP 0 277 366 A1 8/1988

(Continued)

OTHER PUBLICATIONS

Kolobow et al., "A New Thin-Walled Nonkinking Catheter for Peripheral Vascular Cannulation," *Surgery*, vol. 68, No. 4, Oct. 1970, pp. 625-626.

(Continued)

*Primary Examiner* — Nicholas D Lucchesi
*Assistant Examiner* — Laura A Bouchelle
(74) *Attorney, Agent, or Firm* — Seager, Tufte & Wickhem, LLC

(57) ABSTRACT

Composite catheter braids can be formed from a plurality of filaments, some of which can include significant amounts of molybdenum. Filaments including stainless steel and other materials can be used in combination with filaments including molybdenum. Individual filaments can be composed of single metals, or can represent alloys. Composite catheter braids can be employed in intravascular catheters.

19 Claims, 4 Drawing Sheets

U.S. PATENT DOCUMENTS

| | | | |
|---|---|---|---|
| 5,045,072 A | 9/1991 | Castillo et al. | |
| 5,057,092 A | 10/1991 | Webster, Jr. | |
| 5,069,674 A | 12/1991 | Fearnot et al. | |
| 5,078,702 A | 1/1992 | Pomeranz | |
| 5,147,317 A | 9/1992 | Shank et al. | |
| 5,160,559 A | 11/1992 | Scovil et al. | |
| 5,176,660 A | 1/1993 | Truckai | |
| 5,190,520 A | 3/1993 | Fenton, Jr. et al. | |
| 5,217,440 A | 6/1993 | Frassica | |
| 5,219,335 A | 6/1993 | Willard et al. | |
| 5,221,270 A | 6/1993 | Parker | |
| 5,221,372 A | 6/1993 | Olson | |
| 5,234,416 A | 8/1993 | Macaulay | |
| 5,254,107 A | 10/1993 | Soltesz | |
| 5,279,596 A | 1/1994 | Castaneda et al. | |
| 5,306,252 A | 4/1994 | Yutori et al. | |
| 5,318,032 A | 6/1994 | Lonsbury et al. | |
| 5,335,305 A | 8/1994 | Kosa et al. | |
| 5,353,808 A | 10/1994 | Viera | |
| 5,433,200 A | 7/1995 | Fleischhacker, Jr. | |
| 5,441,489 A | 8/1995 | Utsumi et al. | |
| 5,449,372 A | 9/1995 | Schmaltz et al. | |
| 5,454,795 A | 10/1995 | Samson | |
| 5,538,513 A | 7/1996 | Okajima | |
| 5,569,220 A | 10/1996 | Webster, Jr. | |
| 5,573,508 A | 11/1996 | Thornton | |
| 5,603,705 A | 2/1997 | Berg | |
| 5,658,264 A | 8/1997 | Samson | |
| 5,662,622 A | 9/1997 | Gore et al. | |
| 5,664,580 A | 9/1997 | Erickson et al. | |
| 5,667,499 A | 9/1997 | Welch et al. | |
| 5,674,208 A | 10/1997 | Berg et al. | |
| 5,702,373 A | 12/1997 | Samson | |
| 5,720,300 A | 2/1998 | Fagan et al. | |
| 5,728,079 A | 3/1998 | Weber et al. | |
| 5,769,796 A | 6/1998 | Palermo et al. | |
| 5,879,342 A | 3/1999 | Kelley | |
| 5,885,207 A | 3/1999 | Iwasaka | |
| 5,888,436 A | 3/1999 | Keith et al. | |
| 5,891,112 A | 4/1999 | Samson | |
| 5,891,114 A | 4/1999 | Chien et al. | |
| 5,891,191 A | 4/1999 | Stinson | |
| 5,911,715 A | 6/1999 | Berg et al. | |
| 5,927,345 A | 7/1999 | Samson | |
| 5,947,939 A | 9/1999 | Mortier et al. | |
| 5,947,940 A | 9/1999 | Beisel | |
| 5,951,495 A | 9/1999 | Berg et al. | |
| 5,951,539 A | 9/1999 | Nita et al. | |
| 5,954,651 A | 9/1999 | Berg et al. | |
| 5,957,910 A | 9/1999 | Holden, II et al. | |
| 6,019,736 A | 2/2000 | Avellanet et al. | |
| 6,019,786 A | 2/2000 | Thompson | |
| 6,053,903 A | 4/2000 | Samson | |
| 6,053,904 A * | 4/2000 | Scribner et al. | 604/527 |
| 6,068,622 A | 5/2000 | Sater et al. | |
| 6,093,157 A * | 7/2000 | Chandrasekaran | 600/585 |
| 6,096,036 A | 8/2000 | Bowe et al. | |
| 6,096,055 A | 8/2000 | Samson | |
| 6,099,561 A | 8/2000 | Alt | |
| 6,139,511 A | 10/2000 | Huter et al. | |
| 6,143,013 A | 11/2000 | Samson et al. | |
| 6,165,163 A | 12/2000 | Chien et al. | |
| 6,171,295 B1 | 1/2001 | Garabedian et al. | |
| 6,183,508 B1 | 2/2001 | Stinson et al. | |
| 6,186,978 B1 | 2/2001 | Samson et al. | |
| 6,212,422 B1 | 4/2001 | Berg et al. | |
| 6,213,995 B1 | 4/2001 | Steen et al. | |
| 6,245,053 B1 | 6/2001 | Benjamin | |
| 6,245,068 B1 | 6/2001 | Olson et al. | |
| 6,251,092 B1 | 6/2001 | Qin et al. | |
| 6,251,135 B1 | 6/2001 | Stinson et al. | |
| 6,270,496 B1 | 8/2001 | Bowe et al. | |
| 6,290,692 B1 | 9/2001 | Klima et al. | |
| 6,306,105 B1 | 10/2001 | Rooney et al. | |
| 6,340,367 B1 | 1/2002 | Stinson et al. | |
| 6,342,068 B1 | 1/2002 | Thompson | |
| 6,368,316 B1 | 4/2002 | Jansen et al. | |
| 6,379,346 B1 | 4/2002 | McIvor et al. | |
| 6,387,121 B1 | 5/2002 | Alt | |
| 6,395,021 B1 | 5/2002 | Hart et al. | |
| 6,500,203 B1 | 12/2002 | Thompson et al. | |
| 6,505,066 B2 | 1/2003 | Berg et al. | |
| 6,508,806 B1 | 1/2003 | Hoste | |
| 6,517,765 B1 | 2/2003 | Kelley | |
| 6,524,301 B1 | 2/2003 | Wilson et al. | |
| 6,562,022 B2 * | 5/2003 | Hoste et al. | 604/524 |
| 6,626,889 B1 * | 9/2003 | Simpson et al. | 604/524 |
| 6,635,047 B2 | 10/2003 | Forsberg | |
| 6,740,073 B1 | 5/2004 | Saville | |
| 2001/0014770 A1 | 8/2001 | Olson et al. | |
| 2002/0058888 A1 | 5/2002 | Biagtan et al. | |
| 2002/0072729 A1 * | 6/2002 | Hoste et al. | 604/524 |
| 2003/0009184 A1 | 1/2003 | Pepin | |
| 2003/0135114 A1 | 7/2003 | Pacetti et al. | |
| 2003/0216642 A1 | 11/2003 | Pepin et al. | |
| 2004/0181208 A1 | 9/2004 | Poole | |

FOREIGN PATENT DOCUMENTS

| | | |
|---|---|---|
| EP | 0 382 974 A1 | 8/1990 |
| EP | 0 473 045 A1 | 3/1992 |
| EP | 0 732 117 A2 | 9/1996 |
| EP | 0 810 003 A2 | 12/1997 |
| JP | 4-40652 | 4/1992 |
| JP | 5-84303 | 4/1993 |
| WO | WO 93/15785 A1 | 8/1993 |
| WO | WO 96/20750 A1 | 7/1996 |
| WO | WO 96/33763 A2 | 10/1996 |
| WO | WO 00/43061 A1 | 7/2000 |
| WO | WO 01/10492 A1 | 2/2001 |

OTHER PUBLICATIONS

Chapter 7 and Chapter 10, Introduction Magnetic Properties, *Electrical and Magnetic Properties of Metals*, ASM International®, printed on or before May 16, 2002, pp. 193-195 and 263-270.

Ahmed, Salmaan et al., "Magnetic Resonance Imaging Safety: Implications for Cardiovascular Patients," *Journal of Cardiovascular Magnetic Resonance*, vol. 3, No. 3 (2001), pp. 171-182.

Schueler, Beth A. et al., "MRI compatability and Visibility Assessment of Implantable Medical Devices," *Journal of Magnetic Resonance Imaging*, vol. 9 (1999), pp. 596-603.

Spees, William M. et al., "Water Proton MR Properties of Human Blood at 1.5 Tesla: Magnetic Susceptibility, $T_1$, T, $T^*_2$, and Non-Lorentzian Signal Behavior," *Magnetic Resonance in Medicine*, vol. 45 (2001), pp. 533-542.

Teweldemedhin, Z.S. et al., "Magnetic Susceptibility Measurements of Solids," source unknown, dated on or before Jan. 6, 2000, 8 pages.

\* cited by examiner

COMPOSITE CATHETER BRAID

TECHNICAL FIELD

The invention relates generally to catheters and more specifically to catheters having reinforcing braid layers. In particular, the invention relates to catheters having composite braids that include substantial amounts of molybdenum.

BACKGROUND OF THE INVENTION

Reinforcing layers such as reinforcing braid layers can provide thin-walled catheters with kink resistance while retaining a desired level of flexibility. A variety of reinforcing braid constructions are known, providing different combinations of performance characteristics such as flexibility, torque transmission and radiopacity. Nevertheless, a need remains for braids that provide improved performance characteristics, as well as for catheters including such braids.

SUMMARY OF THE INVENTION

The invention is directed to composite catheter braids that incorporate a significant amount of molybdenum, as well as to catheters employing such composite braids.

Accordingly, an example embodiment of the invention can be found in a catheter that has a polymer layer extending from a distal region of the catheter to a proximal region of the catheter. A braid member that includes at least one filament containing a substantial amount of molybdenum is disposed in axial alignment over at least a portion of the polymer layer. The braid includes at least 3 metallic volume percent molybdenum.

Another example embodiment of the invention can be found in a composite braid that includes one or more molybdenum filaments that contain at least about 30 weight percent molybdenum. Each of the molybdenum filaments extend from a proximal end of the braid to a distal end of the braid. The braid includes at least about 3 metallic volume percent molybdenum.

Another example embodiment of the invention can be found in a method of forming a composite catheter braid. A first filament that includes a substantial amount of molybdenum and a second filament that includes stainless steel are provided. The first filament and the second filament can be woven together to form the composite catheter braid.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE PREFERRED EMBODIMENTS

Figure 1:
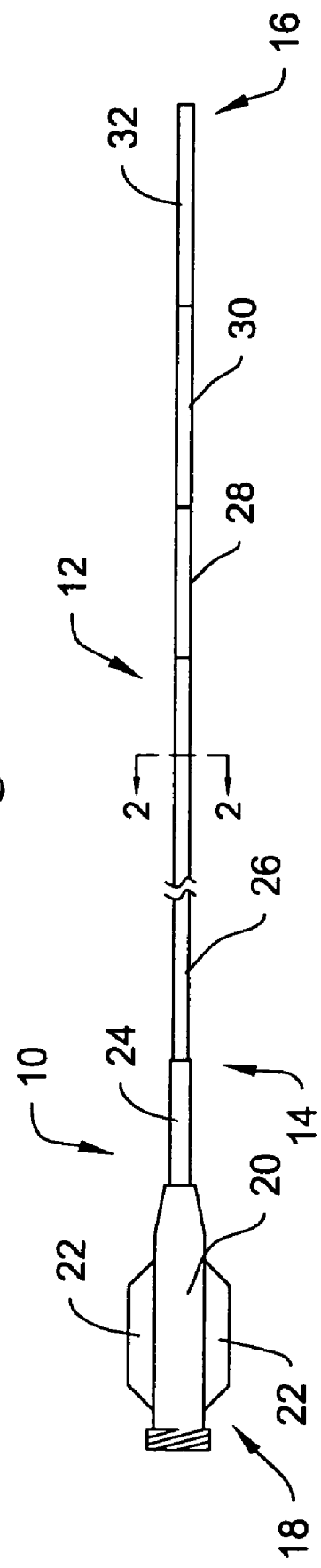
FIG. 1 is a perspective view of an intravascular catheter in accordance with an embodiment of the invention.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the present invention. The catheter 10 can be one of a variety of different catheters, but is preferably an intravascular catheter. Examples of intravascular catheters include balloon catheters, atherectomy catheters, drug delivery catheters, diagnostic catheters and guide catheters. As illustrated, FIG. 1 portrays a guide catheter, but the invention is not limited to such. Except as described herein, the intravascular catheter 10 can be manufactured using conventional techniques.

The intravascular catheter 10 can be sized in accordance with its intended use. The catheter 10 can have a length that is in the range of about 50 centimeters to about 150 centimeters and can have a diameter that is in the range of about 4 F (French) to about 9 F.

In the illustrated embodiment, the intravascular catheter 10 includes an elongate shaft 12 that has a proximal end 14 and a distal end 16. A hub and strain relief assembly 18 can be connected to the proximal end 14 of the elongate shaft 12. The hub and strain relief assembly 18 includes a main body portion 20, a pair of flanges 22 designed to improve gripping, and a strain relief 24 that is intended to reduce kinking. The hub and strain relief assembly 18 can be of conventional design and can be attached using conventional techniques.

The elongate shaft 12 can include one or more shaft segments having varying degrees of flexibility. As illustrated, the elongate shaft 12 includes a first shaft segment 26, a second shaft segment 28, and a third shaft segment 30. In some embodiments, the elongate shaft 12 can include fewer shaft segments or can include more than three segments, depending on the flexibility requirements of a particular application. The elongate shaft 12 also includes a distal tip region 32 that can include an atraumatic distal tip formed from a softer, more flexible polymer.

Figure 2:
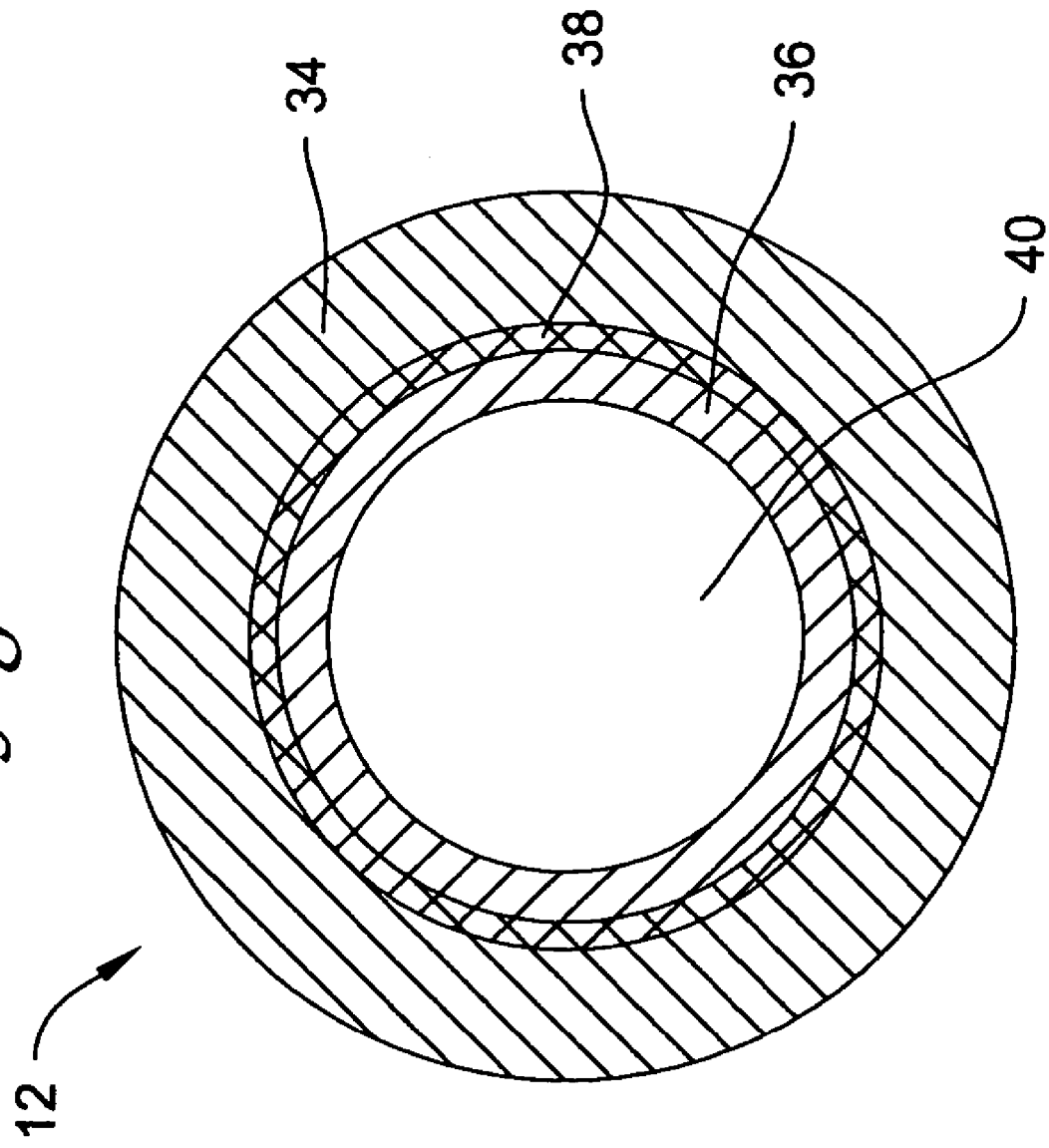
FIG. 2 is a cross-sectional view of the catheter of FIG. 1, taken along line 2-2.

FIG. 2 is a cross-sectional view of the elongate shaft 12, taken along the line 2-2 of FIG. 1. The elongate shaft 12 includes an outer layer 34 and an inner layer 36, and can include a reinforcement layer 38 that is positioned between the inner layer 36 and the outer layer 34. The reinforcement layer is described in greater detail hereinafter. The inner layer 36 defines a lumen 40 that extends through the elongate shaft 12.

Each of the shaft segments 26, 28, 30 can have a similar construction. In particular, each of the shaft segments 26, 28, 30 can include an inner layer 36 and a reinforcing layer 38 that is the same for each of the shaft segments 26, 28, 30 and an outer layer 34 that becomes more flexible in the shaft segments 26, 28, 30 closest to the distal end 16 of the catheter 10. For example, the shaft segment 26 can have an outer layer that is formed from a polymer having a hardness of 72 D (Durometer), the shaft segment 28 can have an outer layer having a hardness of 68 D and the shaft segment 30 can have an outer layer having a hardness of 46 D.

Each of the shaft segments 26, 28, 30 can be sized in accordance with the intended function of the resulting catheter 10. For example, the shaft segment 26 can have a length of about 90 centimeters, the shaft segment 28 and the shaft segment 30 can each have a length in the range of about 1 centimeter to about 3 centimeters. The distal tip region 32 can be formed of any suitable polymer and can have a length of about 5 millimeters.

The inner layer 36 can be a uniform material and can define a lumen 40 that can run the entire length of the elongate shaft 12 and that is in fluid communication with a lumen (not illustrated) extending through the hub assembly 18. The lumen 40 defined by the inner layer 36 can provide passage to a variety of different medical devices, and thus the inner layer 36 can include a lubricious material to reduce friction within the lumen 40. An example of a suitable material includes polytetrafluoro ethylene (PTFE), better known as TEFLON®. The inner layer 36 can be dimensioned to define a lumen 40 having an appropriate inner diameter to accommodate its intended use.

The outer layer 34 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX®), silicones, and co-polymers. The outer layer 34 can be a single polymer, multiple layers, or a blend of polymers. By employing careful selection of materials and processing techniques, thermoplastic, solvent soluble, and thermosetting variants of these materials can be employed to achieve the desired results.

In particular embodiments, a thermoplastic polymer such as a co-polyester thermoplastic elastomer such as that available commercially under the ARNITEL® name can be used. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing layer 38. Part or all of the outer layer 34 can include materials added to increase the radiopacity of the outer layer 34, such as 50% bismuth subcarbonate.

Figure 3:
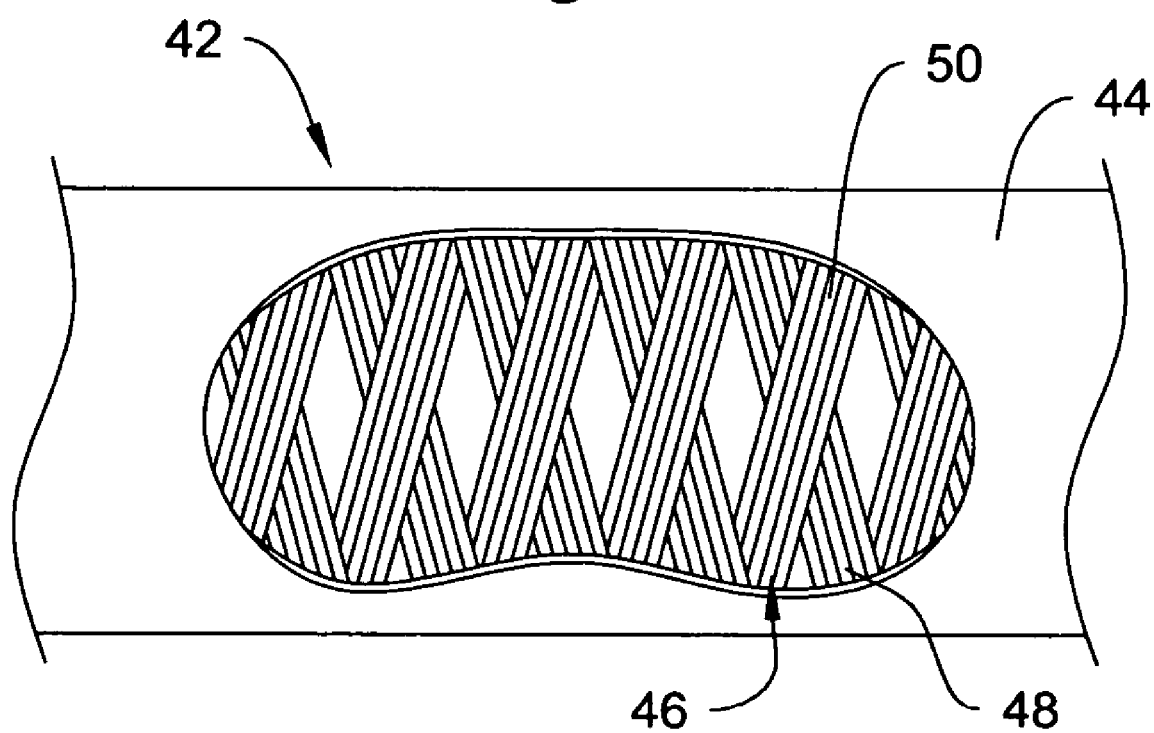
FIG. 3 is a partially sectioned fragmentary view of an intravascular catheter in accordance with an embodiment of the invention.

A reinforcing layer 38 can be positioned between the inner layer 36 and the outer layer 34. A reinforcing braid layer 38 can be formed using a variety of different weave patterns. As illustrated in FIG. 3, which shows a catheter section 42 in which a portion of an outer polymeric layer 44 has been removed, a five-over-five pattern can be used in which five distinct filaments 48 are woven side-by-side in a first direction while another five filaments 50 are woven together side-by-side in a second direction that is different from the first direction. However, other patterns can also be employed. For example, two continuous wires can be woven together in a one-over-one pattern, while other patterns such as a two-over two, three-over-three or a four-over four pattern can be used. In particular embodiments, a sixteen-over-sixteen pattern can be used.

With reference to FIG. 3, a reinforcing layer 46 preferably includes filaments that contain or are formed from molybdenum, preferably at least about 30 weight percent molybdenum in any such filament. The braid can also include metal wires or filaments formed of any suitable material, such as stainless steel, tungsten, gold, titanium, silver, copper, platinum, iridium, or their alloys. The reinforcing layer 46 can also include non-metallic material such as KEVLAR® (poly paraphenylene terephthalamide) fibers, LCP (liquid crystal polymer) fibers, or glass fibers.

Figure 4:
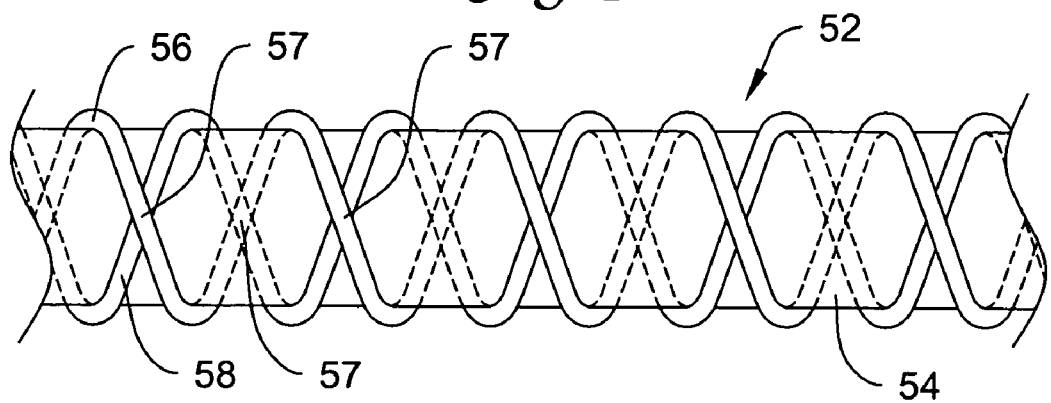
FIG. 4 is a side elevation of a portion of a woven braid in accordance with another embodiment of the invention.

Turning to FIG. 4, a portion of a reinforcing layer 52 is illustrated in which a first filament 56 is woven around a mandrel 54 in a first direction while a second filament 58 is woven around the mandrel 54 in a second direction. Reference to a first filament 56 and a second filament 58 can each refer to a single filament, or can generically refer to a filament aggregate that includes a plurality of single filaments. For example, first filament 56 and/or second filament 58 can each be a filament aggregate containing as many as sixteen single filaments or more. Merely for ease of illustration in FIG. 4, the first filament 56 and the second filament 58 are described and illustrated as single filaments.

In this application, reference to first and second carries no significance other than simply numbering the elements for easy identification. For example, a first direction can be clockwise while a second direction can be counterclockwise.

In some embodiments, as illustrated, the first filament 56 can overlap the second filament 58 at each point at which the first filament 56 contacts or interacts with the second filament 58. These points can be referred to as crossover points. As illustrated in FIG. 4, the first filament 56 can overlap the second filament 58 at a crossover point 57. This configuration can result from weaving the reinforcing layer 52 sequentially, i.e., the second filament 58 is wrapped over the mandrel 54 followed by wrapping the first filament 56.

In other embodiments (not illustrated), the crossover points can vary as a result of weaving the first filament 56 and the second filament 58 around the mandrel 54 at the same time. For example, at a first crossover point, the first filament 56 can overlap the second filament 58, while at an adjacent crossover point the second filament 58 can overlap the first filament 56. In other embodiments, the first filament 56 can overlap the second filament 58 for two or more successive crossover points, followed by the second filament 58 overlapping the first filament 56 at the next two or more successive crossover points.

In preferred embodiments, it is desirable for each of the first filament 56 and the second filament 58 to include or be made of stainless steel or molybdenum, due to the relative strength and flexibility properties of each composition. For instance, molybdenum has an elastic modulus and a density (radiopacity) that is greater than that of stainless steel, while stainless steel can have a tensile strength that is greater than that of molybdenum.

In some embodiments, it is preferred for one of the filaments, say for example the first filament 56, to include or be formed from molybdenum while the other filament, say the second filament 58, to include or be formed from at least one of stainless steel. As illustrated, each of the first filament 56 and the second filament 58 have at least a substantially round cross section. In some embodiments, one or both of the filaments 56 and 58 can have a flat or other non-round cross section.

In some embodiments, the first filament 56 can be formed from a material that includes a substantial amount of molybdenum. In some embodiments, the first filament 56 can include at least 30 weight percent molybdenum. In other embodiments, the first filament 56 can include at least 50 weight percent molybdenum or can even be substantially 100 weight percent molybdenum. In some embodiments, the first filament 56 can be an alloy of molybdenum with any suitable metallic material, such as rhenium. In some embodiments, the first filament 56 can include about 50 to about 100 weight percent molybdenum and up to about 50 weight percent rhenium.

In some embodiments, the second filament 58 can be formed of any suitable metal, including stainless steel. In particular, in some embodiments, the second filament 58 can be formed from a material that is substantially 100 weight percent stainless steel. The second filament 58 can be formed from a material that is an alloy of stainless steel with any other suitable material, such as platinum.

The first filament 56 and the second filament 58 can be formed of materials selected such that the resulting woven braid 52 has an overall materials content that provides a molybdenum content that is at least about 3 metallic volume percent. In some embodiments, the overall molybdenum content can be at least about 8 metallic volume percent, or even about 10 metallic volume percent.

Metallic volume percent can be defined as the volumetric portion of a structure that constitutes a particular material. With respect to braids, metallic volume percent can be defined as the volume of a specific filament of metallic material per unit length of braid divided by the total metallic volume per unit length of braid. If a braid is formed by weaving together a plurality of filaments, with each filament having the same winding density (defined as number of turns per unit length of braid), the metallic volume calculation can be simplified to a comparison of cross-sectional areas.

For example, a 32 filament braid can have 16 filaments woven in a first direction and 16 filaments woven in a second direction. Each of the first direction filaments can have a cross-sectional diameter of 0.002 inches while each of the second direction filaments can have a cross-sectional diameter of 0.001 inches. If eight of the first direction filaments are 100 percent molybdenum, and the remaining 24 filaments are stainless steel, the cross-sectional area of the molybdenum filaments is $2.513 \times 10^{-5}$ square inches, compared to a total cross-sectional area (for all 32 filaments) of $6.284 \times 10^{-5}$ inches. Dividing the former by the latter, followed by multiplying by 100, indicates that the example braid has a molybdenum content of 40 metallic volume percent.

In some embodiments, however, the winding density may not be identical for each filament. In such cases, similar calculations can be carried out by calculating the length of each filament per given length of braid. For the braid just described, assuming a 0.060 inch mandrel diameter and 90 filament crossing points per lineal inch of braid, the length of filament per inch of braid is 1.5 inches. The filament length of 1.5 inches times the cross-sectional area multiplied by 8 molybdenum filaments yields a total molybdenum volume (per inch of braid) of $3.77 \times 10^{-5}$ cubic inches. Dividing by the total filament volume ($9.43 \times 10^{-4}$ cubic inches) yields a ratio of 0.4, or 40 metallic volume percent of molybdenum.

As another example, assume a braid having 16 filaments woven in a first direction and 16 filaments woven in a second direction. The first direction filaments are ribbons with a 0.002 by 0.005 inch cross-section. Two of the first direction filaments are molybdenum while the remaining 14 are stainless steel. The second direction filaments have a 0.0005 by 0.005 inch cross-section and are formed entirely from stainless steel. Given a 0.072 inch mandrel diameter and 90 filament crossing points per lineal inch of braid yields a 1.65 inch filament length per inch of braid. A calculation similar to that above yields a ratio of 0.1 or 10 volume percent molybdenum.

The above illustrative calculations assume that each of the molybdenum filaments are 100 percent molybdenum. In some embodiments, however, the molybdenum filaments can include molybdenum alloys. In these embodiments, the molybdenum volume for a particular filament would be reduced by the volume of other materials present within the filament. For the first example given, with a 40 metallic volume percent molybdenum, if say each of the 8 molybdenum filaments were 50 volume percent molybdenum and 50 volume percent of another metal such as rhenium, the resulting braid would have a 20 metallic volume percent molybdenum content.

Figure 5:
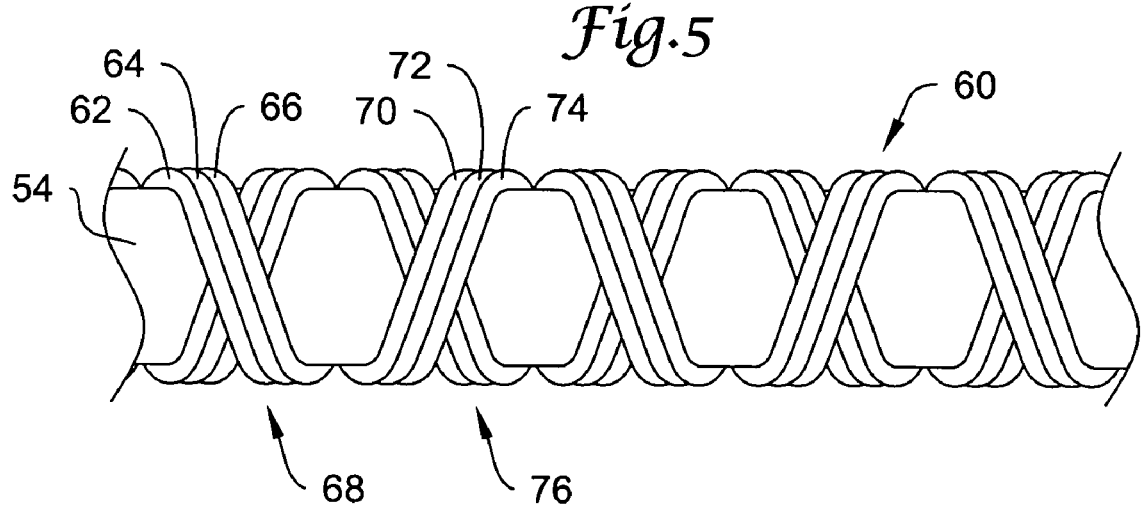
FIG. 5 is a side elevation of a portion of a woven braid in accordance with another embodiment of the invention.

FIG. 5 illustrates a woven braid 60 having a three-over-three pattern. The woven braid 60 is formed from a trio of filaments 62, 64 and 66 woven in a first direction and a trio of filaments 70, 72 and 74 that are woven in a second direction over a mandrel 54. The filaments 62, 64 and 66 together form a filament aggregate 68 while the filaments 70, 72 and 74 form a filament aggregate 76.

In some embodiments, the filament aggregate 68 can include substantially more than the three illustrated filaments 62, 64 and 66. Similarly, the filament aggregate 76 can include substantially more than the three illustrated filaments 70, 72 and 74. In some embodiments, as many as 16 filaments can be woven in a first direction, as the filament aggregate 68 and as many as 16 filaments can be woven in a second direction, as the filament aggregate 76. For ease of illustration, however, only three filaments are shown as part of each of filament aggregate 68 and filament aggregate 76.

As illustrated, the filament aggregates 68 and 76 are woven together such that the filament aggregate 68 overlaps the filament aggregate 76 at a first crossover point (as previously defined), while passing under the filament aggregate 76 at an adjacent crossover point. As discussed above with respect to FIG. 4, this configuration can be achieved by weaving the filament aggregates 68 and 76 simultaneously. In some embodiments, the filament aggregate 68 can overlap the filament aggregate 76 at two or more successive crossover points while the filament 76 can overlap the filament aggregate 68 at the next two or more successive crossover points.

However, the filament aggregates 68 and 76 can also be woven together such that the filament aggregate 68 overlaps the filament aggregate 76 at each crossover point. As noted with respect to FIG. 4, this configuration can be achieved by wrapping the filament aggregates 68 and 76 around the mandrel 54 sequentially. Such a weaving pattern is illustrated, for example, in FIG. 6, which will be discussed in greater detail hereinafter.

Each of the filaments 62, 64 and 66, as well as each of the filaments 70, 72 and 74 can be formed of any suitable material. In some embodiments, it can be desirable for one or more of the filaments 62, 64 or 66 to include or be formed from molybdenum, while others of the filaments 62, 64 and 66 can include or be formed from materials including stainless steel and tungsten. Similarly, one or more of the filaments 70, 72 or 74 can include or be formed from molybdenum, while others of the filaments 70, 72 and 74 can include or be formed from materials including stainless steel and tungsten.

A number of permutations are possible. For example, in the filament aggregate 68, the filament 62 can be substantially 100 weight percent molybdenum, or an alloy of molybdenum with any suitable material, such as rhenium, while each of the filaments 64 and 66 can independently include or be formed from stainless steel, an alloy of stainless steel with any suitable material such as platinum, or tungsten. In some embodiments, for example, the filament 62 can be molybdenum, the filament 64 can be stainless steel, and the filament 66 can be stainless steel. In some embodiments, each of the filaments 62, 64 and 66 can include or be formed from molybdenum. Similarly, in the filament aggregate 76, each of the filaments 70, 72 and 74 can independently include or be formed from one or more of molybdenum, stainless steel, and tungsten.

The filaments 62, 64 and 66 forming the filament aggregate 68 and the filaments 70, 72, and 74 forming the filament aggregate 76 can each be formed of materials selected such that the resulting woven braid 60 has an overall materials content that provides a molybdenum content that is at least 3 metallic volume percent. In some embodiments, the filaments 62, 64 and 66 forming the filament aggregate 68 and the filaments 70, 72, and 74 forming the filament aggregate 76 can each be formed of materials selected such that the resulting woven braid 60 has an overall materials content that provides a molybdenum content that is at least 8 metallic volume percent and in some embodiments can be about 10 metallic volume percent.

As illustrated in FIG. 5, each of the filaments 62, 64 and 66, as well as the filaments 70, 72 and 74, have a substantially round cross section. In some embodiments, the filaments 62, 64, 66, 70, 72 and 74 can have a diameter that is in the range of about 0.0005 inches to about 0.003 inches. In some embodiments, the filaments 62, 64, 66, 70, 72 and 74 can have a diameter that is in the range of about 0.001 inches to about 0.002 inches. In particular embodiments, each of the filaments 62, 64, 66, 70, 72 and 74 can have a diameter that is about 0.0015 inches. In some embodiments, the filaments 62, 64, 66, 70, 72 and 74 can have a flat or other non-round cross section.

Figure 6:
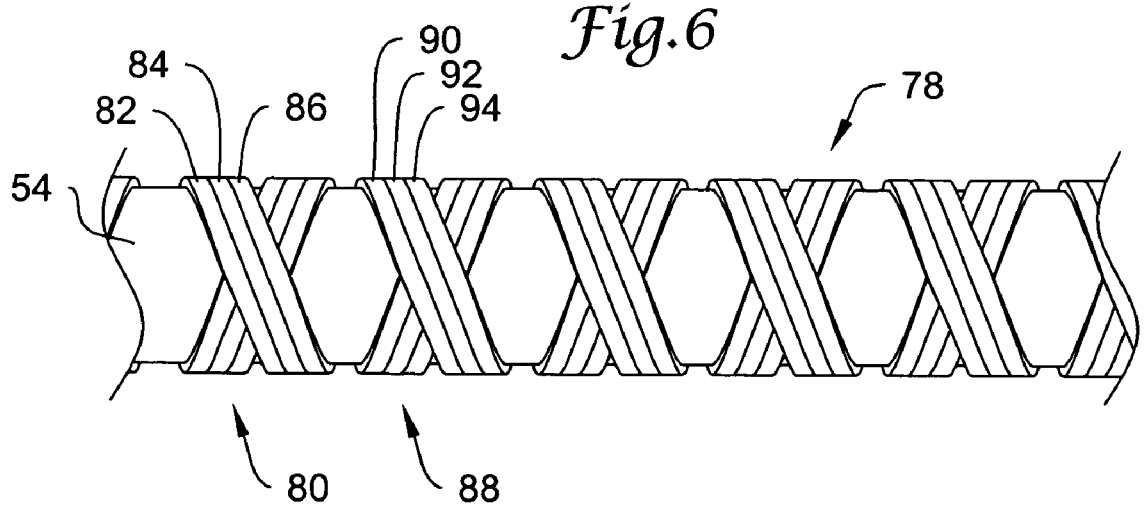
FIG. 6 is a side elevation of a portion of a woven braid in accordance with another embodiment of the invention.

FIG. 6 illustrates a portion of a woven braid 78 positioned over a mandrel 54. A first filament aggregate 80 is composed of three filaments 82, 84 and 86 that are each woven in a first direction. A second filament aggregate 88 is composed of three filaments 90, 92 and 94 that are each woven in a second direction. As illustrated, each of the filaments 82, 84, 86, 90, 92 and 94 have a flat cross section. In other embodiments, one or more of the filaments 82, 84, 86, 90, 92 and 94 can have other cross section shapes including a round cross section.

Each of the filament aggregates 80 and 88 are woven together such that at each crossover point, the filament aggregate 80 overlaps the filament aggregate 88. As discussed above with respect to the braid 60, it is not necessary that the filament aggregates 80 and 88 interact in this manner. In some embodiments, the filament aggregate 80 can overlap the filament aggregate 88 at a first crossover point, while passing under the filament aggregate 88 at an adjacent crossover point. In some embodiments, the filament aggregate 80 can overlap the filament aggregate 88 at two or more successive crossover points while the filament aggregate 88 overlaps the filament aggregate 80 at the next two or more successive crossover points.

As discussed above with respect to FIG. 5, each of the filaments 82, 84 and 86, as well as each of the filaments 90, 92 and 94, can independently include or be formed from any suitable material, including molybdenum, stainless steel or tungsten. A number of permutations are possible. For example, in the filament aggregate 80, the filament 82 can be substantially 100 weight percent molybdenum, or an alloy of molybdenum with any suitable material, such as rhenium, while each of the filaments 84 and 86 can independently include or be formed from stainless steel, an alloy of stainless steel with any suitable material such as platinum, or tungsten.

In some embodiments, for example, the filament 82 can be molybdenum, the filament 84 can be stainless steel, and the filament 86 can be stainless steel. In some embodiments, each of the filaments 82, 84 and 86 can include or be formed from molybdenum. Similarly, in the filament aggregate 88, each of the filaments 90, 92 and 94 can independently include or be formed from one or more of molybdenum, stainless steel, and tungsten.

The filaments 82, 84 and 86 and the filaments 90, 92, and 94 can each be formed of materials selected such that the resulting woven braid 78 has an overall materials content that provides a molybdenum content that is at least 3 metallic volume percent. In some embodiments, the resulting woven braid 78 can have a molybdenum content that is at least 8 metallic volume percent and can be about 10 metallic volume percent.

FIGS. 4 and 5 show filaments 56, 58, 62, 64, 66, 70, 72 and 74 that each have round cross-sections while FIG. 6 illustrates filaments 82, 84, 86, 90, 92 and 94 that each have flat or ribbon-shaped cross-sections. In some embodiments, braids in accordance with the invention can be formed by using a combination of round filaments and flat or ribbon filaments. Some materials may be more easily obtainable in one configuration over another. Ribbon or flat cross section filaments can permit the use of relatively more material without adversely affecting the thickness of the braid.

In some embodiments, a degree of MRI compatibility can be imparted. For example, to enhance compatibility with Magnetic Resonance Imaging (MRI) machines, it may be desirable to make any metallic portions of the catheter 10, such as the reinforcing braid layer 38, or particular embodiments thereof such as the braid 52, the braid 60 and the braid 78, in a manner that would impart a degree of MRI compatibility. For example, the catheter 10, or portions thereof, can be made of a material that does not substantially distort the image and create substantial artifacts (artifacts are gaps in the image). Certain ferromagnetic materials, for example, may not be suitable, because they may create artifacts in an MRI image. Suitable materials include, for example, molybdenum, tungsten, Elgiloy®, MP35N®, nitinol, and the like, and others.

In some embodiments, part or all of the catheter 10 can include a lubricious coating. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of the catheter can be coated with a hydrophilic polymer, while the more proximal portions can be coated with a fluoropolymer.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What I claim is:

1. A catheter having a distal region and a proximal region, the catheter comprising:
   a polymer layer extending from the distal region to the proximal region; and
   a braid disposed in axial alignment with the polymer layer, the braid comprising at least one filament containing a substantial amount of molybdenum, the filament comprising at least about 30 weight percent molybdenum;
   wherein the braid comprises at least about 3 metallic volume percent molybdenum and up to about 10 metallic volume percent molybdenum.

2. The catheter of claim 1, wherein the braid comprises at least about 8 metallic volume percent molybdenum.

3. The catheter of claim 1, wherein the braid comprises about 10 metallic volume percent molybdenum.

4. The catheter of claim 1, wherein the filament comprising a substantial amount of molybdenum comprises up to about 50 weight percent molybdenum.

5. The catheter of claim 1, wherein the filament comprising a substantial amount of molybdenum comprises at least about 50 weight percent molybdenum.

6. The catheter of claim 1, wherein the filament comprising a substantial amount of molybdenum comprises about 100 weight percent molybdenum.

7. The catheter of claim 1, wherein the braid comprises two filaments each containing a substantial amount of molybdenum.

8. The catheter of claim 1, wherein the braid comprises more than two filaments each containing a substantial amount of molybdenum.

9. The catheter of claim 1, wherein the braid further comprises a plurality of filaments containing stainless steel.

10. The catheter of claim 9, wherein the plurality of filaments containing stainless steel comprises about 100 weight percent stainless steel.

11. The catheter of claim 9, wherein the plurality of filaments containing stainless steel comprises stainless steel alloyed with platinum.

12. The catheter of claim 9, wherein the braid comprises a pattern in which 16 first filaments are wrapped in a first direction and 16 second filaments are wrapped in a second direction.

13. The composite catheter braid of claim 12, wherein the first filaments comprise one or more molybdenum filaments and a balance of stainless steel filaments while the second filaments comprise sixteen stainless steel filaments.

14. The composite catheter braid of claim 13, wherein the first filaments each have a diameter of about 0.002 inches while the second filaments each have a diameter of about 0.001 inches.

15. The composite catheter braid of claim 14, wherein the first filaments each comprise ribbons having a cross-section of about 0.002 inches by about 0.005 inches while the second filaments each comprise ribbons having a cross-section of about 0.0005 inches by about 0.005 inches.

16. The composite catheter braid of claim 15, wherein the braid comprises about 10 metallic volume percent of molybdenum.

17. The catheter of claim 1, wherein the polymer layer comprises an inner lubricious liner and the braid is disposed over the inner lubricious liner.

18. The catheter of claim 11, further comprising an outer polymer sheath disposed over the braid.

19. The catheter of claim 1, wherein the at least one filament comprises an alloy of molybdenum and rhenium.

* * * * *